(12) United States Patent
Villarreal

(10) Patent No.: US 11,193,942 B2
(45) Date of Patent: Dec. 7, 2021

(54) METHODS AND DEVICES FOR FEMALE HEALTH MONITORING

(71) Applicant: Anna Villarreal, Brookline, MA (US)

(72) Inventor: Anna Villarreal, Brookline, MA (US)

( * ) Notice: Subject to any disclaimer, the term of this patent is extended or adjusted under 35 U.S.C. 154(b) by 106 days.

(21) Appl. No.: 15/534,218

(22) PCT Filed: Dec. 8, 2015

(86) PCT No.: PCT/US2015/064501
§ 371 (c)(1),
(2) Date: Jun. 8, 2017

(87) PCT Pub. No.: WO2016/094409
PCT Pub. Date: Jun. 16, 2016

(65) Prior Publication Data
US 2017/0363641 A1    Dec. 21, 2017

Related U.S. Application Data

(60) Provisional application No. 62/240,334, filed on Oct. 12, 2015, provisional application No. 62/089,644, filed on Dec. 9, 2014.

(51) Int. Cl.
G01N 33/68    (2006.01)

(52) U.S. Cl.
CPC ..... *G01N 33/6893* (2013.01); *G01N 2800/60* (2013.01)

(58) Field of Classification Search
None
See application file for complete search history.

(56) References Cited

U.S. PATENT DOCUMENTS

| | | | | |
|---|---|---|---|---|
| 6,126,616 A * | 10/2000 | Sanyal | ............... | A61B 10/0291 128/834 |
| 6,174,293 B1 | 1/2001 | Buck et al. | | |
| 6,355,788 B1 * | 3/2002 | Conklin | ............. | C07K 14/4703 435/69.1 |
| 6,548,252 B1 * | 4/2003 | Matson | .................. | C07H 21/04 435/6.14 |
| 6,649,359 B2 | 11/2003 | Mutter et al. | | |
| 7,776,525 B2 | 8/2010 | Kuroda et al. | | |
| 2003/0049244 A1 * | 3/2003 | Seifer | .................... | G01N 33/74 424/94.1 |
| 2003/0113746 A1 | 6/2003 | Leyendecker | | |
| 2005/0215924 A1 * | 9/2005 | Kao | .................... | A61B 10/0045 600/573 |
| 2008/0254048 A1 * | 10/2008 | Cheek | ................ | C07K 16/3069 424/184.1 |
| 2009/0104650 A1 * | 4/2009 | Walton | ............. | G01N 33/56983 435/29 |
| 2012/0040468 A1 * | 2/2012 | Khaled | .............. | A61B 5/14532 436/95 |
| 2012/0094850 A1 * | 4/2012 | Lubenow | ............ | C12Q 1/6881 506/7 |
| 2012/0149017 A1 | 6/2012 | Tabibzadeh et al. | | |
| 2012/0316458 A1 * | 12/2012 | Rahman | ................ | G06F 1/3296 600/549 |
| 2012/0328595 A1 * | 12/2012 | Sun | ....... | A61K 38/179 424/94.5 |
| 2013/0252245 A1 * | 9/2013 | Micallef | ................ | G01N 33/53 435/6.12 |
| 2013/0331666 A1 * | 12/2013 | Miller | ................... | A61B 5/6808 600/309 |
| 2014/0369815 A1 * | 12/2014 | Haller | .................. | F01D 21/003 415/119 |
| 2015/0087935 A1 * | 3/2015 | Davis | ................. | A61B 5/14532 600/309 |
| 2015/0369815 A1 * | 12/2015 | Micallef | .............. | G01N 33/689 514/9.7 |
| 2017/0265789 A1 * | 9/2017 | Naseri | ................ | A61B 10/0045 |
| 2017/0363641 A1 * | 12/2017 | Villarreal | ........... | G01N 33/6893 |
| 2019/0125316 A1 * | 5/2019 | Tariyal | .................... | B01L 3/523 |

OTHER PUBLICATIONS

The International Search Report (PCT/US2015/064501).

* cited by examiner

*Primary Examiner* — Ann Montgomery

(57) ABSTRACT

The present invention relates to, in part, methods of improved healthcare in female subjects that, for example, relay on menstrual fluid sampling for long tem biomarker monitoring.

3 Claims, No Drawings

METHODS AND DEVICES FOR FEMALE HEALTH MONITORING

RELATED APPLICATIONS

This application is a United States National Phase under 35 U.S.C. Section 371 of International Application No. PCT/US2015/064501, filed on Dec. 8, 2015, which claims priority to US Provisional Application Nos. 62/089,644, filed Dec. 9, 2014 and 62/240,334, filed Oct. 12, 2015, the entire contents of all of which are hereby incorporated by reference.

FIELD OF THE INVENTION

This invention relates to, in part, methods and devices that are useful for the treatment, prevention, and/or diagnosis, of various diseases in females, including through repeated monitoring of various disease- or health-related biomarkers.

BACKGROUND

Healthcare is estimated to account for nearly twenty percent of the U.S. GDP—an amount of almost three trillion US dollars. Considering the increased demand for healthcare, resulting from, for instance, increasing population sizes and life expectancies, the magnitude of this industry is expected to rise. With increased demand comes less access to health care practitioners either in the form of, for example, shorter visits or unavailability of appointments. Further, the increased reliance on biomarkers for monitoring patient health and prescribing pharmaceuticals, make accurate biomarker measurements critical for effective health care.

What is needed, are methods, devices, and systems that provide accurate biomarker measurements, while not placing large demands on the health care system.

SUMMARY OF THE INVENTION

Accordingly, the present invention provides methods and devices that enable females to engage in long-term health monitoring of important disease- or health-related biomarkers in a reliable, cost effective, and non-invasive manner.

In one aspect, the invention provides a method for evaluating one or more disease- or health-related biomarkers in a female subject, comprising: (a) obtaining a sample of the female subject's menstrual fluid; (b) measuring the presence, absence, or level of one or more disease- or health-related biomarkers in the sample; and (c) repeating with subsequent menstrual fluid. The trend and/or average levels of the biomarker(s) can be evaluated by the healthcare provider or patient to inform healthcare or life style decisions, including in some embodiments the diagnosis of early stage disease or the state of chronic disease (e.g., controlled or uncontrolled).

In some embodiments, the present methods allow for long term health data that informs a healthcare provider in making healthcare decisions and/or providing improved health care and/or informs a female subject to make improved health/lifestyle decisions. In various embodiments, the method: unnecessary medical care visits, reduces or eliminates unnecessary diagnostic tests, reduces or eliminates unnecessary administration of therapeutic agents, improves the selection of diagnostic tests, and improves the selection of therapeutic agents. Further, in various embodiments, the present methods provide baseline biomarker levels for the patient, as well as long term and short term trends in biomarker levels. Such baseline information or trends allow for more accurate and interpretable diagnostic and/or prognostic tests including, for example, when the baseline or trend health information is used to compare to a biomarker measurement at a single point of time (including, by way of non-limiting example, at a point of care, e.g., upon visit to a healthcare profession presenting symptoms of a disease or disorder).

In various embodiments, the present invention provides a device, such as a disposable cartridge for collecting biomarker information, and optionally inserted or insertable into a wireless enabled device, such as a personal communication device. The invention further provides methods of using cartridges and systems. Accordingly, in various embodiments, the wireless enabled device may link to the cloud and allow secure access to the biomarker information by the patient and one or several healthcare providers and/or diagnostic service providers, or other parties (including health and/or life insurance providers). In some embodiments, the present invention provides a database of the female subject's biomarker information, which may be locally or remotely stored, including cloud-based. Also, in some embodiments, the system comprising the female subject's biomarker information further comprises user interfaces (e.g. graphical user interfaces) that allow controlled and/or secure access to the information. Such interfaces may be accessed via an application on a personal communication device.

In various embodiments, the methods provided herein comprise measurement of various disease- or health-related biomarkers that are used to direct healthcare decisions and/or personal health decisions. In particular, the present invention provides for biomarker measurements for which long term data is desirable. For example, biomarker measurements that are hindered by inconsistency when measured in a single point in time (e.g. point of care) scenario are provided. Further, disease- or health-related biomarkers that are surrogates for slowly developing and/or relatively symptom-free, and/or chronic diseases are provided.

DETAILED DESCRIPTION OF THE INVENTION

The present invention is based, in part, on the discovery that improved healthcare or personal health maintenance for a variety of conditions can be achieved by periodic evaluation of disease- or health-related biomarkers in menstrual fluid.

In one aspect, the invention provides a method for evaluating one or more disease- or health-related biomarkers in a female subject, comprising obtaining a sample of the female subject's menstrual fluid; measuring the presence, absence or level of one or more disease- or health-related biomarkers in the sample, and repeating with subsequent menstrual fluid. The trend and/or average levels of the biomarker(s) can be evaluated by the healthcare provider or patient to inform healthcare or life style decisions (or in some embodiments, decisions of an insurance provider), including in some embodiments the diagnosis of early stage disease or the state of chronic disease (e.g., controlled or uncontrolled).

In various embodiments, the present methods provide for repeated sampling of a female subject's menstrual fluid to allow for an accumulation of data over a period of weeks, months or years. Such data is used to form a more complete subject's health history than standard point of care testing. As described herein, such data allows for an improvement in personal healthcare and/or health decisions.

Also, in some embodiments, the present invention provides for a non-invasive method of monitoring one's health. For example, in various embodiments, the collection of menstrual fluid provides biomarker information without the need for blood draws, biopsies, etc. In some embodiments, the present methods allow for long term health monitoring without various deleterious side effects of standard monitoring including, by way of illustration, excessive bleeding, fainting, lightheadedness, hematoma, infection, pricking or stinging sensations, bruising, pain, throbbing, etc. In some embodiments, the non-invasive nature of the sample collection improves patient compliance and allows for a more complete set of data.

In various embodiments, the evaluation informs a healthcare provider to provide improved health care and/or informs the female subject to make improved health decisions. For example, subtle alterations in one or more disease- or health-related biomarkers over time, away from a normal level, may provide an earlier indication of a disease or disorder than a test at a single point of time (including, by way of non-limiting example, at a point of care) test and before symptoms arise. Further, the repeated evaluations of the present methods allow for early detection of a disease or disorder as the evaluation is not driven by a symptom or sign on the subject part. For instance, the repeated evaluation of menstrual fluid allows for increased healthcare vigilance and largely eliminates the need for reactive medical interventions. In some embodiments, the subject has a chronic disease such as diabetes, congestive heart failure, or multiple sclerosis, and the state (e.g., controlled or uncontrolled) is monitored over time. In some embodiments, the patient has a history, or family history, of cancer, and the method allows recurrence of disease to be closely monitored.

In some embodiments, the evaluation comprises any one of diagnosis, prognosis, and response to treatment. Diagnosis refers to the process of attempting to determine or identify a possible disease or disorder. Prognosis refers to the predicting of a likely outcome of a disease or disorder. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment (e.g. response to a therapeutic agent). Responses to treatment can be, by way of non-limiting example, pathological complete response, survival, and remission.

In various embodiments, the present invention pertains to the generation of a long term health history record that informs care. Accordingly, in various embodiments, the menstrual sample is obtained periodically. In some embodiments, the menstrual sample is obtained on a regular basis. For instance, sampling may occur about once every month, or about once every other month, or about once every 3 months, or about once every 6 months, or about once every 9 months, or about once every year. In some embodiments, about 1 to about 12, or about 2 to about 10, or about 3 to about 8 samples are evaluated per year.

Furthermore, in some embodiments the present methods are repeated long term to generate a large data set. For example, in some embodiments, the evaluation is repeated for about 3 months, or about 6 months, or about 9 months, or about 1 year, or about 2 years, or about 3 years, or about 4 years, or about 5 years, or about 6 years, or about 7 years, or about 8 years, or about 9 years, or about 10 years, or about 20 years, or about 30 years, or about 40 years, or about 50 years.

In various embodiments, the female subject's biomarker information provides baseline health information, as well as long term and short term trends in biomarker levels. In various embodiments, the baseline or trend health information is used to compare to a biomarker measurement at a single point in time (e.g. at the point of care). For example, in various point of care settings, a diagnostic test may not be informative because the single data point being taken may not be reflective of the female subject's condition (e.g. in tests that are prone to data obfuscation by various lifestyle effects, by way of illustration CEA (carcino-embryonic antigen) readings may be skewed by smoking). The present repeated evaluation establishes a baseline or trend value to which comparison can be made. In one embodiment, the female subject is symptomatic for a disease or disorder and a standard single point of time (including, by way of non-limiting example, at a point of care) diagnostic test is taken. Such single point of time test may be a blood test that need not be menstrual fluid. This data is compared to the long term data on the same biological parameter to establish if there is a meaningful change that indicates a disease or disorder. Such information dictates whether further testing is required or if certain treatments should be administered. Accordingly, in some embodiments, the present methods prevent or mitigate incorrect or missed diagnosis. In various embodiments, the present methods allow for one or more of reducing or eliminating unnecessary medical care visits, reducing or eliminating unnecessary diagnostic tests, reducing or eliminating unnecessary administration of therapeutic agents, improving the selection of appropriate diagnostic tests, and improving the selection of appropriate therapeutic agents.

In various embodiments, the present invention relates to various disease- or health-related biomarkers that are available in menstrual fluid. For example, the present invention provides for disease- or health-related biomarkers for which long term data is desirable. Further, in some embodiments, the disease- or health-related biomarkers of the present invention are those which are hindered by inconsistency when measured in a single point of time (including, by way of non-limiting example, at a point of care) scenario. Further still in some embodiments, the present disease- or health-related biomarkers include those which are surrogates for slowly developing and/or relatively symptom-free and/or chronic diseases.

In some embodiments, a panel of disease- or health-related biomarkers is employed. For example, in some embodiments, one or more of the disease- or health-related biomarkers described herein may be evaluated repeatedly. For example, at least 1, or 2, or 3, or 4, or 5, or 6, or 7, or 8, or 9, or 10, or 15, or 20, or 30, or 40, or 50 disease- or health-related biomarkers may be evaluated in a panel.

In various embodiments, the present methods include various disease- or health-related biomarkers including blood cells, vitamins and minerals, blood lipids, steroids, nitrogen markers, tumor antigens, miRNAs, and antibodies.

In various embodiments, the present methods include screening of various blood panels used in routine screening. For example, the present methods may relate to the complete blood count (CBC) panel and/or a blood chemistry panel and/or a blood gas panel. For example, such monitoring may assist in early diagnosis of various conditions, such as anemia, infection, inflammation, bleeding disorders or cancers (e.g. leukemias).

In some embodiments, the present methods relate to repeated blood cell monitoring. For example, the following disease- or health-related biomarkers (including measuring the number, variety, percentage, concentration, and quality of blood cells) may be repeatedly monitored: red blood cells count, hemoglobin, hematocrit, red blood cell indices, MCV (mean corpuscular volume), MCH (mean corpuscular hemoglobin), MCHC (mean corpuscular hemoglobin concentration) are particularly suited for repeated evaluation. For example, monocyte, eosinophil, and basophil counts are rarely informative when taken as a single test; however, a trend of low counts of these cell types can indicate one or more cancers and bone marrow deficiencies, for example.

Illustrative white blood cell evaluations include those listed in the table below. Accordingly, in some embodiments, the biomarker tested, and the condition evaluated, is listed in the following table:

| Biomarker/Test | Illustrative Low Count Conditions | Illustrative High Count Conditions |
|---|---|---|
| WBC<br>White Blood Cell Count | (leukopenia)<br>Bone marrow disorders or damage<br>Autoimmune conditions<br>Severe infections (e.g. sepsis)<br>Lymphoma or other cancer that spread to the bone marrow<br>Diseases of immune system (e.g., HIV) | (leukocytosis)<br>Infection, including bacterial or viral<br>Inflammation<br>Leukemia, myeloproliferative disorders<br>Allergies, asthma<br>Tissue death (e.g. trauma, burns, heart attack)<br>Intense exercise or severe stress |
| Diff<br>White Blood Cell Differential | This test measures the differential totals of each type of WBC and determines if the cells are present in normal proportion to one another, if one cell type is increased or decreased, or if immature cells are present.<br>Illustrative disease or disorders that this may indicate include:<br>Infections caused by, for example, bacteria, viruses, fungi or parasites<br>Inflammation<br>Allergies, asthma<br>Immune disorders (e.g., autoimmune disorders, immune deficiency)<br>Leukemia<br>Myelodysplastic syndrome<br>Myeloproliferative neoplasms | |
| Neu, PMN, polys<br>Absolute neutrophil count, % neutrophils | (neutropenia)<br>infection (e.g. sepsis)<br>Autoimmune disorders<br>Reaction to drugs, chemotherapy<br>Immunodeficiency<br>Myelodysplasia<br>Bone marrow damage (e.g., chemotherapy, radiation therapy)<br>Cancer that spreads to the bone marrow | (neutrophilia)<br>Acute bacterial infections<br>Inflammation<br>Tissue death (e.g. necrosis) caused by trauma, heart attack, burns<br>Certain leukemias (e.g., chronic myeloid leukemia) |
| Lymph<br>Absolute lymphocyte count, % lymphocytes | (lymphocytopenia)<br>Autoimmune disorders (e.g., lupus, rheumatoid arthritis)<br>Infections (e.g., HIV, viral hepatitis, typhoid fever, influenza)<br>Bone marrow damage (e.g., chemotherapy, radiation therapy)<br>Corticosteroids | (lymphocytosis)<br>Acute viral infections (e.g., chicken pox, cytomegalovirus (CMV), Epstein-Barr virus (EBV), herpes, rubella)<br>Certain bacterial infections (e.g., pertussis (whooping cough), tuberculosis (TB))<br>Toxoplasmosis<br>Chronic inflammatory disorder (e.g., ulcerative colitis)<br>Lymphocytic leukemia, lymphoma<br>Stress (acute) |
| Mono<br>Absolute monocyte count, % monocytes | Usually, one low count is not medically significant.<br>Repeated low counts can indicate:<br>Bone marrow damage or failure<br>Hairy cell leukemia | Chronic infections (e.g., tuberculosis, fungal infection)<br>Infection within the heart (e.g. bacterial endocarditis)<br>Collagen vascular diseases (e.g., lupus, scleroderma, rheumatoid arthritis, vasculitis)<br>Monocytic or myelomonocytic leukemia (e.g. acute or chronic) |
| Eos<br>Absolute eosinophil count, % eosinophils | Numbers are normally low in the blood. One or an occasional low number is usually not medically significant | Asthma, allergies such as hay fever<br>Drug reactions<br>Parasitic infections<br>Inflammatory disorders (e.g. celiac disease, inflammatory bowel disease)<br>Some cancers, leukemias or lymphomas |
| Baso<br>Absolute basophil count, % basophils | As with eosinophils, numbers are normally low in the blood; usually not medically significant | Rare allergic reactions (e.g. hives, food allergy)<br>Inflammation (e.g. rheumatoid arthritis, ulcerative colitis)<br>Some leukemias |

Illustrative red blood cell evaluations include those listed in the table below. Accordingly, in some embodiments, the biomarker tested, and the condition evaluated, is listed in the following table:

| Biomarker/Test | Illustrative Low Count Conditions | Illustrative High Count Conditions |
|---|---|---|
| RBC<br>Red Blood Cell Count and/or<br>Hb<br>Hemoglobin and/or<br>Hct<br>Hematocrit | (anemia)<br>Acute or chronic bleeding<br>RBC destruction (e.g., hemolytic anemia, etc.)<br>Nutritional deficiency (e.g., iron deficiency, vitamin $B_{12}$ or folate deficiency)<br>Bone marrow disorders or damage<br>Chronic inflammatory disease<br>Kidney failure | (polycythemia)<br>Dehydration<br>Lung (pulmonary) disease<br>Kidney or other tumor that produces excess erythropoietin<br>Smoking<br>Genetic causes (e.g. altered oxygen sensing, abnormality in hemoglobin oxygen release)<br>Polycythemia vera |
| MCV<br>Mean Corpuscular Volume | Indicates RBCs are smaller than normal (microcytic); caused by iron deficiency anemia or thalassemias, for example. | Indicates RBCs are larger than normal (macrocytic), for example in anemia caused by vitamin $B_{12}$ or folate deficiency |
| MCH<br>Mean Corpuscular Hemoglobin | Mirrors MCV results; small red cells would have a lower value. | Mirrors MCV results; macrocytic RBCs are large so tend to have a higher MCH. |
| MCHC<br>Mean Corpuscular Hemoglobin Concentration | May be low when MCV is low; decreased MCHC values (hypochromia) are seen in conditions such as iron deficiency anemia and thalassemia. | Increased MCHC values (hyperchromia) are seen in conditions where the hemoglobin is more concentrated inside the red cells, such as autoimmune hemolytic anemia, in burn patients, and hereditary spherocytosis, a rare congenital disorder. |
| RDW<br>RBC Distribution Width | Low value indicates uniformity in size of RBCs | Indicates mixed population of small and large RBCs; immature RBCs tend to be larger. For example, in iron deficiency anemia or pernicious anemia, there is high variation (anisocytosis) in RBC size (along with variation in shape—poikilocytosis), causing an increase in the RDW. |
| Reticulocyte Count)<br>Reticulocytes (absolute count or %) | In the setting of anemia, a low reticulocyte count indicates a condition is affecting the production of red blood cells, such as bone marrow disorder or damage, or a nutritional deficiency (e.g. iron, $B_{12}$ or folate) | In the setting of anemia, a high reticulocyte count generally indicates peripheral cause, such as bleeding or hemolysis, or response to treatment (e.g., iron supplementation for iron deficiency anemia) |

Illustrative platelet evaluations include those listed in the table below. Accordingly, in some embodiments, the biomarker tested, and the condition evaluated, is listed in the following table:

| Biomarker/Test | Illustrative Low Count (thrombocytopenia) Conditions | Illustrative High Count (thrombocytosis) Conditions |
|---|---|---|
| Plt<br>Platelet Count | Viral infection (e.g. mononucleosis, measles, hepatitis); Rocky mountain spotted fever; Platelet autoantibody; use of certain drugs (e.g. acetaminophen, quinidine, sulfa drugs); cirrhosis; autoimmune disorders Sepsis; leukemia; lymphoma; myelodysplasia | Cancer (e.g. lung, gastrointestinal, breast, ovarian, lymphoma); rheumatoid arthritis, inflammatory bowel disease; lupus; iron deficiency anemia hemolytic anemia; myeloproliferative disorder (e.g., essential thrombocythemia) |
| MPV<br>Mean Platelet Volume | Indicates average size of platelets is small; older platelets are generally smaller than younger ones and a low MPV may mean that a condition is affecting the production of platelets by the bone marrow. | Indicates a high number of larger, younger platelets in the blood; this may be due to the bone marrow producing and releasing platelets rapidly into circulation. |
| PDW<br>Platelet Distribution Width | Indicates uniformity in size of platelets | Indicates increased variation in the size of the platelets, which may mean that a condition is present that is affecting platelets |

In various embodiments, the disease- or health-related biomarkers of the present invention are one or more of those on a standard blood chemistry panel. Accordingly, in some embodiments, the biomarker tested, and the condition evaluated, is one or more of those described herein. For example, the present methods may include one or more of the following: glucose, uric acid, BUN (blood urea nitrogen) (e.g. for liver and kidney function), creatinine (e.g. for kidney function), BUN/creatinine Ratio (e.g. for impaired renal function), estimated glomerular filtration rate (eGFR), sodium, potassium, chloride, calcium, phosphorus, total protein, albumin, globulin, albumin/globulin ratio, bilirubin (e.g. for kidney and liver function), alkaline phosphatase (e.g. for liver and bone diseases), LDH (lactate dehydrogenase), AST (SGOT) (e.g. for liver function), ALT (SGPT) (e.g. for liver function), iron (serum), and lipid profile (e.g. for the risk for developing atherosclerosis (arterial plaque) and coronary heart disease (including one or more of: total cholesterol, triglycerides, HDL cholesterol, LDL cholesterol, and total cholesterol/HDL ratio)).

In various embodiments, the evaluation is of a blood glucose level and is useful to screen for, diagnose, and monitor high blood glucose (hyperglycemia) or low blood glucose (hypoglycemia), diabetes, and pre-diabetes. For instance, a female subject at risk for type II diabetes may have repeated evaluation of these disease- or health-related biomarkers and such readings may direct lifestyle changes (e.g. increased exercise, improved diet) and/or treatments to avoid an onset or worsening of diabetes (e.g. administration of metformin to control blood glucose levels). Further, the present methods, at least in situations of relatively controlled blood glucose, obviate a need for inconvenient blood glucose monitors that suffer from poor patient compliance due to, in part, their invasiveness (e.g. monitors requiring finger pricking for blood sampling). Further, the biomarker may be HbA1c, which also benefits from repeated evaluation. Normal HbA1c levels are less than 5.7%, pre-diabetes is 5.7% to 6.4%, and diabetes is 6.5% or higher. In some embodiments, the present methods show a gradual increase in HbA1c and allow for lifestyle changes or medical intervention to prevent, for example, the evaluation from normal to pre-diabetes or pre-diabetes to diabetes. Further, it is suggested that diabetic subjects maintain an HbA1c level of less than about 7% and the present methods allow for an uninvasive manner to monitor this. For example, if the periodic evaluations show HbA1c levels rising to 7% or above, medical intervention of lifestyle change may be ordered to mitigate detrimental effects (e.g. increased likelihood or onset of one or more of eye disease, heart disease, kidney disease, nerve damage, and stroke).

In some embodiments, the present methods allow for repeated evaluation of vitamin and/or mineral disease- or health-related biomarkers, including, for example, those listed in the table below. Accordingly, in some embodiments, the biomarker tested, and the condition evaluated, is listed in the following table:

| Vitamin and/or Mineral Biomarker | Indication |
|---|---|
| vitamin A | Essential for vision |
| | Keeps tissues and skin healthy |
| | Plays an important role in bone growth |
| | Lowers lung cancer risk |
| | Carotenoids act as antioxidants |
| | Protects against cataracts |
| thiamin (vitamin $B_1$) | Needed for healthy skin, hair, muscles, and brain |
| riboflavin (vitamin $B_2$) | Needed for healthy skin, hair, blood, and brain |
| niacin (vitamin $B_3$, nicotinic acid) | Essential for healthy skin, blood cells, brain, and nervous system |
| pantothenic acid (vitamin $B_5$) | Helps make lipids, neurotransmitters, steroid hormones, and hemoglobin |
| vitamin $B_6$ (pyridoxal, pyridoxine, pyridoxamine) | Aids in lowering homocysteine levels and reduces the risk of heart disease |
| | Helps convert tryptophan to niacin and serotonin, and therefore important for sleep, appetite, and mood, for example |
| | Helps make red blood cells |
| | influences cognitive abilities and immune function |
| vitamin $B_{12}$ (cobalamin) | Aids in lowering homocysteine levels and lowers the risk of heart disease |
| | Assists in making new cells and breaking down some fatty acids and amino acids |
| | Protects nerve cells and encourages their normal growth |
| | Helps make red blood cells |
| biotin | Helps metabolism and synthesis of glucose and some fatty acids |
| | Needed for healthy bones and hair |
| vitamin C (ascorbic acid) | Lowers the risk for some cancers, including, for example, those of the mouth, esophagus, stomach, and breast |
| | Protects against cataracts |
| | Helps make collagen, and therefore assists in wound healing wounds and supports blood vessel walls |
| | Helps in synthesis of neurotransmitters serotonin and norepinephrine |
| | Acts as an antioxidant, neutralizing unstable molecules that can damage cells |
| | Bolsters the immune system |
| choline | Helps make and release the neurotransmitter acetylcholine, which aids in many nerve and brain activities |
| | Plays a role in metabolizing and transporting fats |
| vitamin D (calciferol) | Helps maintain normal blood levels of calcium and phosphorus, which, among others, strengthen bones and teeth |
| | Can reduce the number of non-spinal fractures |
| vitamin E (alpha-tocopherol) | Acts as an antioxidant, neutralizing unstable molecules that can damage cells |
| | Protects vitamin A and certain lipids from damage |
| | Helps prevent Alzheimer's disease |
| | Protects against prostate cancer |

-continued

| Vitamin and/or Mineral Biomarker | Indication |
| --- | --- |
| folic acid (folate, folacin) | Lowers levels of homocysteine and reduces heart disease risk |
| | Reduces risk for colon cancer |
| | Offsets breast cancer risk among women who consume alcohol |
| vitamin K (phylloquinone, menadione) | Activates proteins and calcium essential to blood clotting |
| | Helps prevent hip fractures |
| calcium | Builds and protects bones and teeth |
| | Helps with muscle contractions and relaxation, blood clotting, and nerve impulse transmission |
| | Plays a role in hormone secretion and enzyme activation |
| | Helps maintain healthy blood pressure |
| chloride | Balances fluids in the body |
| | Essential to digestion |
| chromium | Enhances the activity of insulin, helps maintain normal blood glucose levels, and is needed to free energy from glucose |
| copper | Plays an important role in iron metabolism |
| | Helps make red blood cells |
| fluoride | Encourages strong bone formation and tooth maintenance |
| iodine | Part of thyroid hormone, which helps set body temperature and influences nerve and muscle function, reproduction, and growth |
| | Prevents goiter and a congenital thyroid disorder |
| iron | Helps hemoglobin in red blood cells and myoglobin in muscle cells ferry oxygen throughout the body |
| | Needed for biosynthesis of amino acids, collagen, neurotransmitters, and hormones |
| magnesium | Works with calcium in muscle contraction, blood clotting, and regulation of blood pressure |
| | Helps build bones and teeth |
| manganese | Helps form bone |
| | Helps metabolize amino acids, cholesterol, and carbohydrates |
| molybdenum | Part of several enzymes, one of which helps ward off a form of severe neurological damage in infants that can lead to early death |
| phosphorus | Helps build and protect bones and teeth |
| | Part of DNA and RNA |
| | Part of phospholipids, which carry lipids in blood and help shuttle nutrients into and out of cells |
| potassium | Balances fluids in the body |
| | Helps maintain steady heartbeat and send nerve impulses |
| | Needed for muscle contractions |
| | lowers blood pressure |
| | benefits to bone structures |
| selenium | Acts as an antioxidant |
| | Helps regulate thyroid hormone activity |
| sodium | Balances fluids in the body |
| | Helps send nerve impulses |
| | Needed for muscle contractions |
| | Impacts blood pressure |
| sulfur | Protein synthesis and folding |
| | Needed for healthy hair, skin, and nails |
| zinc | Helps form many enzymes and proteins and create new cells |
| | Frees vitamin A from storage in the liver |
| | Needed for immune system, taste, smell, and wound healing |
| | When taken with certain antioxidants, zinc delays the progression of age-related macular degeneration |

Such repeated evaluation allows for early detection of one or more deficiencies or excesses that can be mitigated with nutritional supplements or dietary changes, for example. Further, such repeated monitoring is useful to prevent the effects of long term vitamin and/or mineral imbalance (e.g. calcium deficiencies leading to, for example, bone maladies such as osteoporosis and/or hypocalcemia).

In some embodiments, the biomarker is one or more disease- or health-related biomarkers measured in a blood gas test. For instance, the female subject may have pH evaluated repeatedly. Such evaluations may be used to detect an acid-base imbalance, such as can occur with kidney failure, heart failure, uncontrolled diabetes, and infections. pH may be used along with other tests, such as electrolytes to determine if an electrolyte imbalance is present, glucose to evaluate blood sugar concentrations, and BUN and creatinine tests to evaluate kidney function.

In some embodiments, the biomarker is C-reactive protein (CRP). This biomarker may be repeatedly evaluated to establish health information related to levels of inflammation, which is central to a number of diseases or disorders, including without limitation coronary heart disease, diabetes, macular degeneration, and cognitive decline. Measurement of CRP is predictive of a risk of incident myocardial infarction, stroke, peripheral arterial disease, and sudden cardiac death among healthy individuals with no history of cardiovascular disease, and predictive of recurrent events and death in patients with acute or stable coronary syndromes. Further, increased levels of C-reactive protein have been strongly linked with a greater risk of developing type II diabetes. Reliable and early detection of rising CRP can allow for appropriate intervention with diet, supplements, or anti-inflammatory therapy before onset significant health detriments. Illustrative lifestyle changes which may be directed by observed increases in CRP include the use of one or more of omega-3 supplements (e.g. fish oil, krill oil, etc.), L-carnitine, and soluble fiber before meals.

In some embodiments, the biomarker is fibrinogen, which plays a role in blood clotting and increases in response to tissue inflammation. Since the development of atherosclerosis and heart disease are essentially inflammatory processes, increased fibrinogen levels can help predict the risk of heart disease and stroke. High fibrinogen levels not only are associated with an increased risk of heart attack, but also are seen in other inflammatory disorders such as rheumatoid arthritis and glomerulonephritis. A repeated evaluation of fibrinogen levels helps prevent or mitigate any of these diseases or disorders. A combination of lifestyle and behavioral changes—such as quitting smoking, losing weight, and becoming more physically active—may be directed by the present monitoring. Further, increases in fibrinogen may direct one or more nutritional interventions, such as omega-3 supplements (e.g. fish oil, krill oil, etc.), niacin, and folic acid, and vitamins A and C.

In some embodiments, the biomarker is dehydroepiandrosterone (DHEA), a hormone produced by the adrenal glands, which is a precursor to the sex hormones estrogen and testosterone. Blood levels of DHEA peak in one's twenties and then decline dramatically with age, decreasing to 20-30% of peak levels between the ages of 70 and 80. DHEA is frequently referred to as an "anti-aging" hormone. Healthy levels of DHEA may support immune function, bone density, mood, libido, and healthy body composition. Elevated levels of DHEA may indicate congenital adrenal hyperplasia, a group of disorders that result from the impaired ability of the adrenal glands to produce glucocorticoids. Supplementation with DHEA increases immunological function, improves bone mineral density, increases sexual libido in women, reduces abdominal fat, protects the brain following nerve injury, and helps prevent diabetes, cancer, and heart disease. Natural therapies may help to optimize DHEA levels, e.g. pregnenolone or DHEA. Accordingly, DHEA is a biomarker for which repeated evaluation is beneficial.

In some embodiments, the biomarker is thyroid stimulating hormone (TSH), which controls thyroid hormone secretion in the thyroid. When blood levels fall below normal, this indicates hyperthyroidism (also called thyrotoxicosis), and when values are above normal, this suggests hypothyroidism. Overt hyper- or hypothyroidism is generally easy to diagnose, but subclinical disease can be more elusive and therefore repeated evaluation is beneficial. Further, because the symptoms of thyroid imbalance may be nonspecific or absent and may progress slowly, and since many doctors do not routinely screen for thyroid function, mild hyper- or hypothyroidism can go undiagnosed for some time. Undiagnosed mild disease can progress to clinical disease states. Mild hypothyroidism (low thyroid gland function) may be associated with reversible hypercholesterolemia (high blood cholesterol) and cognitive dysfunction, as well as such nonspecific symptoms as fatigue, depression, cold intolerance, dry skin, constipation, and weight gain. Mild hyperthyroidism is often associated with atrial fibrillation (a disturbance of heart rhythm), reduced bone mineral density, and nonspecific symptoms such as fatigue, weight loss, heat intolerance, nervousness, insomnia, muscle weakness, shortness of breath, and heart palpitations. Accordingly, the use of the present methods may allow for early detection to avoid or mitigate diseases or disorders related to TSH imbalance. In some embodiments, further supplementation with one or more of L-tyrosine, iodine, and selenium may be directed by the present methods.

In some embodiments, the biomarker is homocysteine. High homocysteine levels have been associated with increased risk of heart attack, bone fracture, and poor cognitive function. Further, incremental increases in the level of homocysteine correlate with an increased risk for coronary artery disease, indicating a benefit of repeated evaluation. Homocysteine has also become recognized as an independent risk factor for bone fractures. The present methods may inform the use of vitamin $B_{12}$, vitamin $B_6$, folic acid, and trimethylglycine to optimize homocysteine levels.

In some embodiments, the biomarker is a blood ketone. This biomarker may be useful to monitor the development of monitor diabetic ketoacidosis (DKA) in female subjects with type 1 and sometimes type 2 diabetes. DKA is associated with acute hyperglycemia, a severe insulin deficiency, and a disruption of the body's acid-base balance.

In some embodiments, the biomarker is relevant to cancer diagnosis, prognosis or treatment response. For example, a female subject may be repeatedly screened for one or more known cancer biomarker. By way of illustration, the cancer disease- or health-related biomarkers of the present invention include those listed in the table below. Accordingly, in some embodiments, the biomarker tested, and the condition evaluated, is listed in the following table:

| Tumor Biomarker | Illustrative Associated Cancer(s) | Comments |
|---|---|---|
| AFP (Alpha-feto protein) | Certain cancers of the liver, ovaries and testes | Also elevated during pregnancy and acute and chronic hepatitis |
| $\beta_2$M (Beta-2 microglobulin) | Multiple myeloma, chronic lymphocytic leukemia (CLL), and some lymphomas | Elevated in other conditions, such as kidney disease |
| BCR-ABL | Chronic myeloid leukemia (CML) and BCR-ABL-positive acute lymphocytic leukemia (ALL) | |
| CA 15-3 (Cancer antigen 15-3), e.g. via CA 15-3 or CA 27.29 | Breast | Also elevated in other cancers, including lung, ovarian as well as benign breast conditions, endometriosis, hepatitis |
| CA 19-9 (Cancer antigen 19-9) | Pancreatic, sometimes bile ducts, gallbladder, stomach, colon | Also elevated in other forms of digestive tract cancer and non-cancer, thyroid disease, pancreatitis, bile duct obstruction, and inflammatory bowel disease |

-continued

| Tumor Biomarker | Illustrative Associated Cancer(s) | Comments |
| --- | --- | --- |
| CA-125 (Cancer antigen 125) | Ovarian | Also elevated with other cancers such as endometrial, peritoneal, fallopian tube, and non-cancers such as endometriosis, PID, some other benign diseases and conditions such as uterine fibroids, pregnancy |
| Calcitonin | Medullary thyroid carcinoma (MTC) and C-cell hyperplasia | Also elevated with other cancers, such as lung cancers and leukemias |
| CEA (Carcino-embryonic antigen) | Colorectal as well as pancreatic, lung, breast, ovarian, medullary thyroid or other cancers | Elevated in conditions such as RA, hepatitis, COPD, colitis, pancreatitis, and in cigarette smokers |
| Chromogranin A (CgA) | Neuroendocrine tumors (carcinoid tumors, neuroblastoma) | Highly sensitive tumor marker for carcinoid tumors |
| DCP (Des-gamma-carboxy prothrombin) | Hepatocellular carcinoma (HCC) | |
| Gastrin | G-cell hyperplasia, gastrin-producing tumor (gastrinoma) | Also used to help diagnose Zollinger-Ellison syndrome |
| hCG (Human chorionic gonadotropin, also called Beta-hCG) | Testicular and trophoblastic disease, germ cell tumors, choriocarcinoma | Elevated in pregnancy |
| JAK2 mutation | Certain types of leukemia | Also used to diagnose bone marrow disorders characterized by overproduction of one or more types of blood cells known as myeloproliferative neoplasms (MPNs), especially polycythemia vera (PV) |
| LD (Lactate dehydrogenase) | Testicular and other germ cell tumors | LDH is elevated in a wide variety of conditions and is often used to help identify the cause and location of tissue damage in the body and to monitor its progress; may be used in other cancers, such as lymphoma, melanoma, neuroblastoma. |
| Monoclonal immunoglobulins | Multiple myeloma and Waldenstroms macroglobulinemia | Cloned plasma cell with overproduction of one type of immunoglobulin, may be detected by protein electrophoresis or serum free light chains |
| SMRP (Soluble mesothelin-related peptides) | Mesothelioma (rare type of cancer associated with asbestos exposure) | Often used in conjunction with imaging tests |
| Thyroglobulin | Thyroid | |

For example, in some embodiments, the biomarker is CEA. In some embodiments, a rise in CEA over the course of periodic evaluations is indicative of a disease or disorder. Such a biomarker may be repeatedly evaluated in instances in which a female subject may be afflicted with various cancers. For example, such subjects may have a family history of these cancers, be a cancer survivor that is testing for recurrence, etc. CEA may be monitored for colorectal, pancreatic, lung, breast, ovarian, urinary tract, medullary thyroid or other cancers. Further, a rise in CEA may be indicative of RA, hepatitis, COPD, colitis, pancreatitis, inflammation, cirrhosis, peptic ulcer, ulcerative colitis, rectal polyps, emphysema, benign breast disease.

This biomarker is illustrative of a need for repeated evaluation. For example, the levels of CEA increase in certain conditions and/or lifestyle choices and thus run the risk of false positive data (and, in turn, possible unnecessary further testing or treatment). By way of non-limiting example, CEA levels may be obfuscated by one or more of cigarette smoking, liver and gallbladder problems (e.g. cirrhosis and/or cholecystitis), inflammatory bowel diseases (such as ulcerative colitis or diverticulitis), lung infection(s), inflammation of the pancreas (pancreatitis) and stomach ulcer. For instance, the normal range of CEA is about 0-2.5 mcg/L, while in cigarette smokers the normal range is about 0-5 mcg/L. The present methods establish a baseline of biomarker levels that correct for biomarker aberrations related to certain conditions and/or lifestyle choices. In this example, repeated testing would correct for CEA elevation associated with smoking. For instance, if a smoker has a CEA test, the repeated evaluation of the present methods would allow for a health practitioner to note that a high value is really the smoker's baseline value.

In some embodiments, the female subject may repeatedly be evaluated for one or more cancer markers to which the female subject is susceptible. For example, the female subject may have a family medical history which includes one or more hereditary cancers, such as breast cancer, colorectal cancer, ovarian cancer, pancreatic cancer, stomach cancer, and uterine cancer. Further, the female subject may be a cancer survivor who is repeatedly evaluated for one or more disease- or health-related biomarkers for the early detection of recurrence.

In various embodiments, the female subject is repeatedly evaluated for one or more disease- or health-related biomarkers associated with breast cancer. For instance, such a female subject may be one who previously had breast cancer and/or has a family history of breast cancer. For instance, the female subject may apply the methods described herein to monitor for breast cancer recurrence. Illustrative disease- or health-related biomarkers to be evaluated include one or more of estrogen receptor (ER), progesterone receptor (PR). Such evaluation is indicative of, if afflicted with breast cancer, a likelihood of response to one or more hormone therapies, such as tamoxifen (NOLVADEX), the presence of the disease- or health-related biomarkers indicating a higher likelihood of response. Another biomarker of interest, especially in the context of breast cancer is human epidermal growth factor receptor 2 (HER2), which is indicative of, if afflicted with breast cancer, a likelihood of response to anti-HER2 treatments, such as trastuzumab (HERCEPTIN), and in some cases, may suggest whether additional treatment with chemotherapy may be helpful. Another biomarker of interest, especially in the context of breast cancer is one or more of cancer antigen 15-3 (CA 15-3), cancer antigen 27.29 (CA 27.29), and carcinoembryonic antigen (CEA). These disease- or health-related biomarkers are particularly informative of an occurrence of metastatic cancer but may also be helpful in the diagnosis and/or prognosis of, for example, inflammation, cirrhosis, peptic ulcer, ulcerative colitis, rectal polyps, emphysea, and benign breast disease. Yet another biomarker of interest, especially in the context of breast cancer is one or more of urokinase plasminogen activator (uPA) and plasminogen activator inhibitor (PAI-1). Higher-than-normal levels of these tumor markers in the cancer tissue may mean that the cancer is more aggressive (e.g. faster growing). Further, these tumor markers may be used to guide the use of chemotherapy after surgery for patients with node-negative breast cancer.

In various embodiments, the female subject is repeatedly evaluated for one or more disease- or health-related biomarkers associated with colon or colorectal cancer. For instance, such a female subject may be one who previously had colon or colorectal cancer and/or has a family history of colon or colorectal cancer. For instance, the female subject may apply the methods described herein to monitor for colon cancer recurrence. Illustrative disease- or health-related biomarkers include those described in *Mol Diagn Ther.* 2011 Jun. 1; 15(3):129-41 or *World J Gastrointest Oncol* 2014 April 15; 6(4): 83-97, the contents of which are hereby incorporated by reference in their entirety. In some embodiments, the biomarker is methylated Septin 9 DNA ("'SEPT9), and an increase in this biomarker is indicative or an occurrence of high likelihood of occurrence of colon cancer. In some embodiments, including those testing RNA, the biomarker is one or more of ANXA3, CLEC4D, LMNB1, PRRG4, TNFAIP6, AND VN1, the overexpression of which is indicative or an occurrence of high likelihood of occurrence of colon cancer and IL2RB the reduced expression of which is indicative or an occurrence of high likelihood of occurrence of colon cancer.

In various embodiments, the female subject is repeatedly evaluated for one or more disease- or health-related biomarkers associated with ovarian cancer. For instance, such a female subject may be one who previously had ovarian cancer and/or has a family history of ovarian cancer. For instance, the female subject may apply the methods described herein to monitor for ovarian cancer recurrence. In many women with ovarian cancer, levels of CA-125 are high and therefore this biomarker is included in the present methods. In various embodiments, the biomarker for ovarian cancer of the present methods is one or more of Table 2 of Cortesi et al. *Electrophoresis* 2011, 32, 1-12, the entire contents of which are hereby incorporated by reference. For instance, the biomarker for ovarian cancer of the present methods may be one or more Retinoblastoma-binding protein 4, Elongation factor 1-a 1, Malate dehydrogenase mitochondrial, Glyceraldehyde-3-phosphate dehydrogenase, Osteoglycin, Annexin 5, Hydroxyacyl-coenzyme A dehydrogenase mitochondrial, proteasome activator complex subunit 2, Galectin-3, Calcium-activated neutral proteinase small subunit 1, Glutathione-S-transferase Mu-3, Peroxiredoxin-6, Triosephosphate isomerase, Adenylate kinase 3, Tumor protein D52, Rho GDP dissociation inibitor 1, Apolipoprotein A-I, Serum amyloid P-component, Glutathione-S-transferase Mu2, Glutathione-S-transferase Mu1, Glutathione-S-transferase Mu1, Flavin reductase, Peroxiredoxin-1, Cleavage and polyadenilation specificity factor 5 subunit Glutathione S-transferase A2, Adenylate kinase isoenzyme 1, Transgelin, Translationally-controlled tumor protein, Lactoylglutathione lyase, Synthase subunit d, mitochondrial, Ubiquitin-conjugatin enzyme E2 K, Glutathione-S-transferase P1, Abhydrolase domin-containing protein 14B, Phosphatidylethanolamine-binding protein 1, Peptidyl-prolyl cis-trans isomerase B, Heat shock protein b 6, Cytochrome b5, Eukariotic translation initiation factor 5A-1, Transthyretin, Ubiquitin-conjugatin enzyme E2 N Retinol binding protein, Galectin-1, Hemoglobin subunit b, Hemoglobin subunit b, Profilin 1 Hemoglobin subunit a, Protein S 100-A8-calgranulin A, Protein S 100-A8-calgranulin A, b-2 microglobulin Histone H4, Protein S 100-A6 Peroxiredoxin-1, Ubiquitin, Superoxide dismutase, Heat shock protein b 1, Abhydrolase domain containing protein 11 GTP-binding nuclear protein Ran, and Superoxide dismutase (Mn) mitochondrial. In various embodiments, the biomarker for ovarian cancer of the present methods is one or more of Tables 4 or 5 of *Gynecologic Oncology* 108 (2008) 402-408, the entire contents of which are hereby incorporated by reference, In various embodiments, the female subject is repeatedly evaluated for one or more disease- or health-related biomarkers associated with pancreatic cancer. For instance, the female subject may apply the methods described herein to monitor for pancreatic cancer recurrence. For instance, such a female subject may be one who previously had pancreatic cancer and/or has a family history of pancreatic cancer. For instance, the female subject may have a CA 19-9 (Cancer antigen 19), as part of the repeated evaluation. Further, CEA (Carcinoembryonic antigen) may be monitored. Further, elevation of amylase over time may be indicative of pancreatic cancer.

In various embodiments, the female subject is repeatedly evaluated for one or more disease- or health-related biomarkers associated with lung cancer. For instance, such a female subject may be one who previously had lung cancer and/or has a family history of lung cancer. For instance, the female subject may apply the methods described herein to monitor for lung cancer recurrence.

In some embodiments, the biomarker is a matrix metalloproteinase such as matrix metalloproteinase-2 (MMP-2), -9 (MMP-9), and -13 (MMP-13) and the cancer is colorectal and/or bladder cancer.

In some embodiments, the biomarker is circulating tumor DNA (ctDNA), namely, genome fragments that float freely through the bloodstream.

In various embodiments, the female subject is repeatedly evaluated for one or more disease- or health-related biomarkers associated with endometriosis. Endometriosis is a gynecological disease defined as the presence of endometrial tissue outside the uterine cavity. This tissue is located in the peritoneum, ovary or fallopian tube and more rarely in the pleura, lung or brain. Endometriosis occurs in 5-20% of females with pelvic pain, 20-50% of infertile females and 6-10% of females of reproductive age. The causes of this disease include, among others, retrograde menstruation, endometrium abnormalities, peritoneal environment changes, increased angiogenesis, inadequate immunological reactions and genetic and environmental factors. In various embodiments, the present invention relates to the evaluation of endometriosis, for instance by measuring one or more of annexin V, VEGF, CA-125, sICAM-1/or glycodelin, MIF, CD74, IL-6, IL-8 and COX-2 may be evaluated using the samples and methods of the present invention) (see, e.g., *Hum Reprod.* 2012 September; 27(9):2698-711, *Fertil Steril.* 2015 January; 103(1):153-9.e3, *Hum Reprod.* 2010 March; 25(3):654-64, the entire contents of which are hereby incorporated by reference). In various embodiments, the present invention relates to the evaluation of endometriosis, for instance by measuring one or more of octamer-binding transcription factor 4 (Oct-4), C-X-C chemokine receptor type 4 (CXCR4), SRY-box containing gene 2 (SOX2) and mesenchymal-epithelial transition factor (MET), collapsin response mediator protein 2 (CRMP2), ubiquitin carboxyl-terminal hydrolase isozyme L1 (UCH-L1) and myosin regulatory light polypeptide 9 (MYL9 may be evaluated using the samples and methods of the present invention) (see, e.g., *Molecular Medicine Reports* 8: 183-188, 2013, the entire contents of which are hereby incorporated by reference).

In some embodiments, a female subject is evaluated for a variety of disease- or health-related biomarkers that relate to delusion or hallucination. For example, a female subject with a family history of psychiatric disorders or diseases. For example, one or more disease- or health-related biomarkers found in, for example, Table 5A, Table 5B, Table 6A, and Table 6B of US Patent Publication No. 2011/0098188, the contents of which are hereby incorporated by reference in their entirety, are useful. In some embodiments, the genes Drd2, ApoE, Nab1, Idh1, Scamp1, Ncoa2, Aldh1l1, Gpm6b are evaluated and a decrease in expression is indicative of a higher likelihood of high delusions states or the genes Nrg1, Egr1, Dctn1, Nmt1, Pllp, Pvalb, Nmt1, Pctk1 are evaluated and an increase in expression is indicative of a higher likelihood of high delusions states. Accordingly, the repeated evaluation may direct the administration of anti-psychotic agents as known in the art.

In some embodiments, the biomarker is the brain protein tau. This biomarker may be used as an indicator of brain injuries, for example, concussions. For example, the female subject may be an athlete that monitors brain status to avoid long term complications associated with concussions (e.g. memory problems, lack of inhibition, intense anger and/or aggression, personality changes, inattention and lack of concentration, problems organizing, planning, and problem solving, and language impairment).

In some embodiments, the biomarker is one that is informative for heart health, such as one or more troponins (e.g. a cardiac-specific troponin I or troponin T test), CK-MB, and myoglobin.

In various embodiments, the present methods relate to monitoring for signs of Alzheimer's disease. For instance, the female subject may have relatives with Alzheimer's disease and may monitor Alzheimer's blood markers repeatedly, including for example, IRS-1 and tau.

Liver damage, including liver fibrosis and cirrhosis, may be monitored with the present methods. For example, aspartate transaminase and alanine transaminase may be measured as disease- or health-related biomarkers. For example, a AST/ALT ratio, the ratio between the concentrations of aspartate transaminase (AST) (aspartate aminotransferase) and alanine transaminase (ALT) (alanine aminotransferase), in the blood is useful to differentiate between causes of liver damage, or hepatotoxicity. Further, blood cell monitoring, including complete blood counting, may be indicative of liver function.

Further, in some embodiments, the biomarker is alpha-fetoprotein (AFP) and is useful for long term evaluation of liver diseases or disorders (e.g. hepatitis). Increases in AFP are associated with hepatocellular carcinoma, germ cell tumors, and metastatic cancers of the liver.

In various embodiments, the biomarker is one or more antibodies that may, for example, reflect an infection. For example, IgA, IgD, IgE, IgG and IgM, may be measured over time and increases may be indicative of increased immunological activity. For example, if a female subject is suspected of having Lyme disease and shows increases in IgM and/or IgG, that rise over time, then it is likely that the person has an active *B. burgdorferi* infection. Further antibodies can be used to indicate affliction with one or more of Multiple myeloma and Waldenström macroglobulinemia.

In various embodiments, the biomarker is one or more steroids. For example, in some embodiments, the biomarker is cortisol. Different diseases, such as Cushing syndrome and Addison disease, can lead to either too much or too little production of cortisol. Measuring blood cortisol level can help diagnose these conditions. It is also measured to evaluate how well the pituitary and adrenal glands are working. Further, cortisol may be used to measure long term stress and indicate lifestyle changes are necessary.

In various embodiments, the biomarker is one or more of the biomarkers listed in the table below. In some embodiments, the biomarker of the left-most column is useful in the evaluation of a subject, by way of non-limitation, by evaluation of menstrual fluid from the patient, for a disease in the column labelled "illustrative disease." In various embodiments, the biomarker of the left-most column is used in the diagnosis, or prognosis, or evaluation of response to treatment of the illustrative disease. The references of the below table are hereby incorporated by reference in their entirety, especially as to descriptions linking the enumerated biomarker to the enumerated disease. In various embodiments, one or more (e.g. 1, or 2, or 3, or 4., or 5, or 6, etc.) of the illustrative biomarkers can be used in the evaluation of a patient for an illustrative disease. By way of non-limiting example, in some embodiments, evaluation of Activin A and follistatin can be used to evaluate endometrial function including the diseases below as well as dysfunctional uterine bleeding (see, e.g., *Reprod Sci.* 2007 May; 14(4):383-9, the entire contents of which are hereby incorporated by reference). In some embodiments, inhibin and activin is evaluated in the context of ovarian cancer e.g. as a measure in diagnosis and management and also as a factor in the pathogenesis of these tumors (see, e.g., *Endocr Relat Cancer.* 2004 March; 11(1):35-49, the entire contents of which are hereby incorporated by reference). In another embodiment, follistatin (FST) and CA-125 can be used to evaluate ovarian cancer (and, by way of non-limitation, reduce the number of false-positive results in diagnosis) (see, e.g., *J Int Med Res.* 2012; 40(3):877-86, the entire contents of which are hereby incorporated by reference). Further, in some embodiments, follistatin (FST) and BRCA1 can be used to evaluate ovarian cancer and human ovarian surface epithelial cells (see, e.g., *PLoS One.* 2012; 7(6):e37697, the entire contents of which are hereby incorporated by reference). Further, in some embodiments, follistatin (FST) and activin A can be used to evaluate peritoneal, ovarian and deep infiltrating endometriosis (see, e.g., *Human Reproduction*, Vol. 00, No. 0 pp. 1-7, 2009 doi:10.1093/humrep/dep195, the entire contents of which are hereby incorporated by reference). In some embodiments, EMMPRIN and fascin may be used in the evaluation of ovarian cancer, including differential diagnosis of some diagnostically problematic mucinous ovarian tumors (see, e.g., *Pathol Res Pract.* 2014 December; 210(12):934-8, the entire contents of which are hereby incorporated by reference).

| Biomarker/Protein Name | Illustrative Activity | Illustrative Disease | Reference |
| --- | --- | --- | --- |
| Activin A | Promotion of migratory and invasive potential | ovarian cancer lung cancer | Endocrinology. 2008 August; 149(8): 3809-3816 |
| FST: FS-288, FS-300, and FS-315/ Follistatin | cellular proliferation | ovarian cancer, ovarian endometrioma | Human Reproduction, Vol. 00, No. 0 pp. 1-7, 2009 doi: 10.1093/humrep/dep195 |
| Inhibin-A, Inhibin-B/Inhibin | inhibitory activities involved in proliferation and differentiation of many organ systems. | ovarian cancer breast cancer | GYNECOLOGIC ONCOLOGY 69, 23-31 (1998); Endocr Relat Cancer Feb. 1, 2014 21 R51-R65 |
| CTNNB1/Beta-Catenin (Catanin beta-1) | cell-cell adhesion, epithelial to mesenchymal transition, proto-oncogene | ovarian cancer | Integrin Regulation of β-Catenin Signaling in Ovarian Carcinoma J Biol Chem. 2011 Jul. 1; 286(26) |
| p-akt/protein kinase b | promotes survival and growth | ovarian cancer | Mol Cancer Ther. 2007 January; 6(1): 334-345 |
| p-gsk3b/Glycogen synthase kinase 3b | tumorigenesis | ovarian cancer | Endocrinology. 2008 August; 149(8): 3809-3816. |
| fgf2/fibroblast growth factor 2 | angiogenesis | ovarian cancer | Oncogene (2004) 23, 8171-8183 |
| CDH1/e-cadherin | cell proliferation, cell-cell binding | PID breast cancer | Clin Chim Acta. 2014 Apr. 20; 431: 118-24 |
| IL-1/6/interleukin 1 and 6 | hematopoietic stem cells differentiation, inflammatory responses | ovarian cancer endometriosis | Journal of Ovarian Research 2010, 3: 3 |
| GTPase K-Ras/V-Ki-ras2 Kirsten rat sarcoma viral oncogene homolog | transmission of cell-growth-promoting signals from the cell surface receptors | ovarian cancer lung cancer | Journal of Biomedicine and Biotechnology Volume 2010 (2010), Article ID 150960 |
| N-Cadherin | cell-cell adhesion | ovarian cancer | Gynecol Oncol. 2004 July; 94(1): 16-24. |
| cxcr4/C-X-C chemokine receptor type 4, or fusin, or CD184 | receptor with potent chemotactic activity for lymphocytes | ovarian cancer | |
| arhi (DIRAS3)/Aplasia Ras homolog member I | induces autophagy in ovarian cancer cells | ovarian cancer | Cell Death and Differentiation (2014) 21, 1275-1289 |
| Stat3/Signal transducer and activator of transcription 3 | cell growth and apoptosis | ovarian cancer | |
| P21WAF1/CIP1/cyclin-dependent kinase inhibitor 1 or CDK-interacting protein 1 | inhibits the activity of cyclin-CDK2, -CDK1, and -CDK4/6 complexes, and thus functions as a regulator of cell cycle progression at G1 and S phase. | ovarian cancer | protein expression in primary ovarian cancer. (2000) December 1231-1236 |
| Jak1/Janus kinase 1 | critical role in initiating responses to multiple major cytokine type 1 and 2 receptor families | ovarian cancer | |
| MMP-9/Matrix metallopeptidase 9 (MMP-9), also known as 92 kDa type IV collagenase, 92 kDa gelatinase or gelatinase B (GELB) | involved in the degradation of the extracellular matrix, tumor progression, including invasion, metastasis, growth and angiogenesis | ovarian cancer | |
| TCTP/Translationally controlled tumour protein | tumorigenesis, proliferation, cell-death prevention | ovarian cancer | |
| AGR2/Anterior gradient protein 2 homolog (AGR-2), also known as secreted cement gland protein XAG-2 homolog | plays a role in protein folding, cell migration, cell differentiation and cell growth | ovarian cancer breast cancer | Exp Mol Med. 2011 Feb. 28; 43(2): 91-100; breast cancer res. 2013 Apr. 24; 15(2): 204 |
| PRSS8/Prostasin | epithelial sodium channel regulator | ovarian cancer | Journal of Oncology Volume 2012 (2012), Article ID 709049 |

-continued

| Biomarker/Protein Name | Illustrative Activity | Illustrative Disease | Reference |
| --- | --- | --- | --- |
| VEGF/Vascular endothelial growth factor | vasculogenesis and angiogenesis | ovarian cancer, endometriosis | Women's Health Vol. 9, No. 2, Pages 171-187; Hum Reprod. 2012; 27(9): 2698-2711. |
| Wnt5A/Protein Wnt-5A | secreted cell signaling molecules that regulate cell to cell interactions, cell-fate, motility | ovarian cancer | Oncol Rep. 2014 August; 32(2): 771-9. |
| CD164/Sialomucin core protein 24 or endolyn | tumorigenecity, proliferation, adhesion, and differentiation of hematopoietic stem cells | ovarian cancer | |
| ACTB/Actin, cytoplasmic 1 | cell motility, structure and integrity | ovarian cancer | Mol Cell Proteomics. 2012 October; 11(10): 1024-1035. |
| APOH/Beta-2-glycoprotein 1 | associated with excessive clotting | unexplained blood clotting | The Test Beta-2 Glycoprotein 1 Antibodies Sep. 2, 2015 |
| CLTC/clathrin heavy chain 1 | intracellular trafficking of receptors and endocytosis of a variety of macromolecules | | |
| FIBG/FGG/Fibrinogen gamma chain | regulate cell adhesion and spreading, display vasoconstrictor and chemotactic activities, and are mitogens for several cell types | Various cancers | |
| FLNA/Filamin-A | helps build the network of protein filaments (cytoskeleton) that gives structure to cells and allows them to change shape and move | Glioblastoma multiforme | |
| HP/Haptoglobin | disease progression | ovarian cancer | Journal of Ovarian Research Proteomic identification of fucosylated haptoglobin alpha isoforms in ascitic fluids BioMed Central Sep. 2, 2015 |
| HBB/Hemoglobin subunit beta | HBB interacts with Hemoglobin, alpha 1 (HBA1) to form haemoglobin A | ovarian cancer | Cancer Sci. 2005 March; 96(3): 197-201. |
| IHRP/inter-alpha-trypsin inhibitor family heavy chain-related protein | inhibits polymerization through binding to actin and protects cells from phagocytosis. | ovarian cancer | |
| MIF/Macrophage migration inhibitory factor | enhances tumor growth, progression, and angiogenesis, | ovarian cancer | |
| A2MG, or A2M/Alpha-2-macroglobulin | protease inhibitor in mammals | ovarian cancer | |
| FIBB/Fibrinogen beta chain | tumorigenesis, blood clot formation cascade | ovarian cancer | |
| HBA/Hemoglobin subunit alpha | HBA interacts with Hemoglobin, alpha 1 (HBA1) to form haemoglobin A | ovarian cancer | |

-continued

| Biomarker/Protein Name | Illustrative Activity | Illustrative Disease | Reference |
|---|---|---|---|
| HBD/Hemoglobin subunit delta | HBD interacts with Hemoglobin, alpha 1 (HBA1) to form haemoglobin A | pancreatic cancer | |
| HBG1/Hemoglobin subunit gamma-1 | HBG1 is a fetal subunit component of hemoglobin | beta-thalassemia | |
| H4//histone H4 | direct the configuration of chromatin and so access by transcription factors | ovarian cancer | |
| ENOA/Alpha-enolase | hypoxic condition, ENOA act as a stress protein that is up-regulated via activation of the transcription factor hypoxia-inducible factor-1 (HIF-1) and may provide protection to the cells by increasing anaerobic metabolism | ovarian cancer | |
| CO3/C3/Complement C3 | stimulates tumor cell growth | ovarian cancer | |
| TRFE/Serotransferrin | promoter of tumor development and survival via antiapoptotic effects | ovarian cancer | |
| CERU/Ceruloplasmin | important roles in iron metabolism and antioxidant defense (25). Ceruloplasmin blocks the copper ion-activated production of toxic oxygen compounds and protects cells from oxidative stress | germ-line ovarian cancer | |
| IC1/Plasma protease C1 inhibitor | regulates vascular permeability and suppression of inflammation | ovarian cancer | |
| PLMN/Plasminogen | tumor invasion and metastasis | ovarian cancer | |
| PROF1/Profilin-1 | regulate actin polymerization in response to extracellular signals | ovarian cancer | |
| ACTBL/Beta-actin-like protein 2 | cell motility, structure and integrity. Alpha actins are a major constituent of the contractile apparatus | ovarian cancer | |
| HBG2/Hemoglobin subunit gamma-2 | HBB interacts with Hemoglobin, alpha 1 (HBA1) to form haemoglobin A | ovarian cancer | |
| SAA4/Serum amyloid A-4 protein | tumorigenesis | ovarian cancer | |
| A2ML1/Alpha-2-macroglobulin-like protein 1 | protease inhibitor in mammals | ovarian cancer | |

| Biomarker/Protein Name | Illustrative Activity | Illustrative Disease | Reference |
|---|---|---|---|
| H12/Histone H1.2 | condensation of nucleosome chains into higher-order structured fibers. Acts also as a regulator of individual gene transcription through chromatin remodeling, nucleosome spacing and DNA methylation | ovarian cancer | |
| FSCN1/Fascin | cell migration - actin filament bundling protein | Hodgkin's disease breast cancer (inc. triple negative) ovarian cancer NSCLC (inc. metastasis) urothelial carcinoma of the bladder pancreatic ductal adenocarcinoma (PDAC) colorectal cancer | |
| PEBP1/Phosphatidylethanolamine-binding protein 1 | plays a pivotal modulatory role in several protein kinase signaling cascades | hepatocellular carcinoma | Hepatology, November 2010 Volume 53, Issue 5, Pages 872-879 |
| ALBU/Serum albumin | serve as carriers for molecules of low water solubility this way isolating their hydrophobic nature, including lipid-soluble hormones, bile salts, unconjugated bilirubin, free fatty acids (apoprotein), calcium, ions (transferrin), and some drugs like warfarin, phenobutazone, clofibrate & phenytoin | breast cancer | BBA Clinical Volume 2, December 2014, Pages 24-30 |
| TPM1/Tropomy alpha-1 chain | regulating the function of actin filaments in both muscle and nonmuscle cells | ovarian cancer | Journal of Proteome Research (Impact Factor: 5). May 2007; 6(4): 1440-50. |
| TPM4/Tropomy alpha-4 chain | stabilizes cytoskeletin actin filaments | breast cancer | CANCER GENOMICS & PROTEOMICS 12: 89-102 (2015) |
| VIME/Vimentin | supports and anchors the position of the organelles in the cytosol | breast cancer | Cell Mol Life Sci. 2011 September; 68(18): 3033-3046. |
| WDR1/WD repeat-containing protein 1 | Facilitate formation of heterotrimeric or multiprotein complexes. Members of this family are involved in a variety of cellular processes, including cell cycle progression, signal transduction, apoptosis | breast cancer | |
| ANXA5/Annexin A5 | indirect inhibitor of the thromboplastin-specific complex | endometriosis | Hum Reprod. 2012; 27(9): 2698-2711. |

| Biomarker/Protein Name | Illustrative Activity | Illustrative Disease | Reference |
| --- | --- | --- | --- |
| PROP/Properdin | participates in some specific immune responses. It plays a part in tissue inflammation as well as the engulfing of pathogens | endometriosis | Hum Reprod Update. 2010 November-December; 16(6): 651-674. |
| B2MG/Beta-2-microglobulin | protein binding | endometriosis | Hum Reprod Update. 2010 November-December; 16(6): 651-674. |
| G3P, GAPDH/Glyceraldehyde-3-phosphate dehydrogenase | cellular iron homeostasis, catalyzes the 6th step of glycolysis | ovarian cancer | |
| ANGI/Angiogenin | potent stimulator of new blood vessels through the process of angiogenesis | endometriosis | Hum Reprod Update. 2010 November-December; 16(6): 651-674. |
| PON1/Serum paraoxonase/arylesterase 1 | enzyme capable of hydrolysing a wide variety of substrates | endometriosis | Hum Reprod Update. 2010 November-December; 16(6): 651-674. |
| HGFA/Hepatocyte growth factor activator | activates hepatocyte growth factor regulates cell growth, cell motility, and morphogenesis | endometriosis | Hum Reprod Update. 2010 November-December; 16(6): 651-674. |

In various embodiments, the biomarker is follistatin. Follistatin (FST) is a monomeric glycoprotein that inhibits release of follicle-stimulating hormone from the pituitary. It is a specific binding protein of activin and is involved in the regulation of multiple physiological and pathological functions, and has important roles in early embryonic development, differentiation of ovarian granulosa cells, liver fibrosis and polycystic ovarian syndrome. FST's levels vary with physiological and pathological conditions such as pregnancy and cancer. Follistatin circulates in two major isoforms: a full-length molecule composed of 315 amino acids (FS315), and a short isoform of 288 amino acids (FS288) generated by alternative splicing of the Fst gene. The activin/follistatin system is thought to act primarily as a local growth regulator system controlling proliferation, differentiation and apoptosis of many cell types in an autocrine and paracrine manner. Of interest is the full expression of the activin/follistatin system in human endometrium. Activin A stimulates the decidualization of endometrial stromal cells and aberrant expression of the activin/follistatin axis has been observed in the endometria of women with recurrent miscarriage (*Fertil Steril* 2006; 86:1723-1730, the entire contents of which are hereby incorporated by reference), anovulatory bleeding (*Reprod Sci* 2007; 14:383-389., the entire contents of which are hereby incorporated by reference) and endometriosis (*Aust N Z J Obstet Gynaecol* 2006; 46:148-153., the entire contents of which are hereby incorporated by reference). In various embodiments, the present invention relates to the measurement of FST, e.g. in menstrual fluid, in the context of evaluating one or more of the diseases described herein.

In various embodiments, the biomarker is activin A. The activins are a family of proteins which consist of disulphide-linked homodimers and heterodimers of the β subunits of inhibin termed $\beta_A$ and $\beta_B$. These three proteins, called activin A ($\beta_A$-$\beta_A$), activin B ($\beta_B$-$\beta_B$) and activin AB ($\beta_A$-$\beta_B$), are members of the transforming growth factor β (TGFβ) super-family of proteins. Although the activins were originally isolated for their ability to stimulate follicle-stimulating hormone secretion, they have been shown to influence many biological processes, including parenchymal haemopoiesis, embryogenesis, neurotransmission, hepatic parenchymal cell division, prostate biology and angiogenesis. In various embodiments, evaluation of cancers via activin, e.g. as described in *Cancers* 2015, 7, 70-91, the entire contents of which are hereby incorporated by reference, is provided. In various embodiments, the present invention relates to the measurement of activin A, e.g. in menstrual fluid, in the context of evaluating one or more of the diseases described herein.

In various embodiments, the biomarker is CA-125. CA-125 has found application as a tumor marker or biomarker that may be elevated in the blood of some patients with specific types of cancers, or other benign conditions. CA 125 is most consistently elevated in epithelial ovarian cancer, but can be expressed in a number of gynecologic (e.g. endometrial, fallopian tube) and non-gynecologic (pancreatic, breast, colon and lung) cancers. The best established application of the CA 125 assay is in monitoring ovarian cancer. The rate of decline in CA 125 during primary chemotherapy has been an important independent prognostic factor in several multivariate analyses. Persistent elevation of CA 125 at the time of a second look surgical surveillance procedure predicts residual disease with >95% specificity. Rising CA-125 values have preceded clinical detection of recurrent disease by at least 3 months in most, but not all studies. Rising CA 125 during subsequent chemotherapy has been associated with progressive disease in more than 90% of cases. In various embodiments, the present invention relates to the measurement of CA-125, e.g. in menstrual fluid, in the context of evaluating one or more of the diseases described herein.

In various embodiments, the biomarker is fascin. Fascin is an actin-bundling protein that has a major function in forming parallel actin bundles in cell protrusions such as lamellipodia, which are key specializations of the plasma membrane for cell migration. Fascin overexpression has been reported in many different types of carcinomas, including breast, colon, pancreas, esophagus, stomach, lung, and urinary bladder, as well as in other tumors, such as lymphomas, sarcomas, melanomas, and astrocytomas. The high expression of fascin is correlated with an aggressive clinical course and shorter survival. Fascin organizes actin into highly dynamic and architecturally diverse subcellular scaffolds. These scaffolds orchestrate a variety of mechanical processes, including filopodial protrusions in motile cells. In various embodiments, the present invention relates to the measurement of fascin, e.g. in menstrual fluid, in the context of evaluating one or more of the diseases described herein.

In some embodiments, the present invention relates to a device for collection of a female subject's menstrual fluid sample and uses thereof. In some embodiments, the device is a disposable cartridge which may be inserted into a wireless enabled device. In various embodiments, the device is a home instrument. In various embodiments, the device is operated by the patient, without the need for intervention by a medical professional. Accordingly, in various embodiments, the patient is spared the inconvenience of scheduling an appointment in a medical clinical and may be able to institute sample collection at her convenience and without scheduling delays.

In various embodiments, the device is or comprises a sampling implement that provides a means to collect a sample from a subject. The sampling implement may be connected to a collection chamber via a sampling implement holder. In some embodiments, the sampling implement is disposed at the distal end of a shaft, which shaft can be solid, hollow or semi-permeable. In some embodiments, the sampling implement is a swab, a comb, a brush, a spatula, a rod, a foam, a flocculated substrate or a spun substrate.

In various embodiments, the device is associated with and/or integrated into one or more of a tampon, pad (menstrual napkin) or menstrual cup (see, e.g., International Patent Publication Nos. WO/2002/080827 and WO/2006/058409, the contents of which are hereby incorporated by reference).

In various embodiments, the collection of menstrual fluid may take place on one of the heaviest days of the donor's menstrual period which may be the first or second day. In various embodiments, the general area around the vagina may be cleansed with an aseptic cleaning pad prior to collection.

In various embodiments, a single sample or multiple samples may be collected. The sample or samples may be maintained at room temperature (about 15° C. to about 25° C.). In various embodiments, samples may be shipped to a laboratory so long as the sample or samples arrive at the laboratory within about 24 hours to about 72 hours of collection. Alternatively, samples may be refrigerated at about 1° C. to about 10° C.

In various embodiments, the sample may be subjected to centrifugation and either the supernatant or pellet may be analyzed.

In various embodiments, the evaluation comprises measuring a presence, absence, or level of a protein. In various embodiments, the evaluation comprises measuring a presence, absence, or level of expression of a nucleic acid.

In some embodiments, the present methods comprise contacting an agent that specifically binds a biomarker with the menstrual sample. For example, such an agent may be an antibody. Illustrative, but non-limiting methods for evaluation include one or more of immunohistochemical staining, western blotting, in cell western, immunofluorescent staining, ELISA, and fluorescent activating cell sorting (FACS), or any other method described herein or known in the art.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, N Y, 1988), Harlow et al. (Using Antibodies, A Laboratory Manual, Cold Spring Harbor Laboratory, N Y, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a $F(ab)_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid.

A person skilled in the art will appreciate that a number of methods can be used to detect or quantify the DNA/RNA levels of various disease- or health-related biomarkers.

Gene expression can be measured using, for example, low-to-mid-plex techniques, including but not limited to reporter gene assays, Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP.

A person skilled in the art will appreciate that a number of methods can be used to detect or quantify the level of RNA products of the disease- or health-related biomarkers within a sample, including arrays, such as microarrays, RT-PCR (including quantitative PCR), nuclease protection assays and Northern blot analyses.

In various embodiments, the present methods allows for efficient transfer of healthcare information between medical practitioners. For example, any of the methods and systems of US Patent Publications Nos. 2014/0164022, 2013/0060574, and 2007/0135690, the contents of which are hereby incorporated by reference in their entirety, may be used.

In some embodiments, the method provides a database of the female subject's biomarker information. In various embodiments, the database is locally or remotely stored. In various embodiments, the database is cloud-based. In various embodiments, the database can be stored and/or transferred via physical transport media, for example on a USB thumb drive, tablet or phone, CD ROM, or smart card, and/or via transport media, secure transmission can occur via a network line, or wireless cell phone communication, Internet, ultrasound, Bluetooth, or near-field communication.

In various embodiments, the database comprises a subject interface and/or a healthcare provider interface, the interfaces optionally being graphical user interfaces (GUIs). In various embodiments, the subject interface and/or a healthcare provider interface is accessible via an application on a personal communication device, optionally selected from a laptop computer, a tablet computer, a personal digital assistant (PDA), and a smart phone. Personal communication device include, for example, IPHONES (available from Apple Inc., Cupertino, Calif.), BLACKBERRY devices (available from Research in Motion, Waterloo, Ontario, Canada), or any smart phones equipped with the ANDROID platform (available from Google Inc., Mountain View, Calif.), tablets, such as the IPAD and KINDLE FIRE, and personal digital assistants (PDAs).

In various embodiments, the healthcare provider may be the female subject's physician or female subject's physician's associates and/or the healthcare provider may be personnel from laboratory that processes the female subject's menstrual fluid sample. In various embodiments, data flows to and from the database, for example, via wireless cell phone communication, Internet, ultrasound, Bluetooth, or near-field communication.

In various embodiments, the database is protected by automatic logoff, which is required by HIPAA Either the subject-side software or the wireless LAN or both will initiate automatic logoff to disconnect a user after a pre-configured period of time of inactivity.

In various embodiments, the database not only stores the female subject's biomarker information but also provides suggestions of lifestyle changes based on such information. These suggestions may be entered by a healthcare provider or automatically generated from medical databases (e.g. via wireless cell phone communication, Internet, ultrasound, Bluetooth, or near-field communication, such as WEBMD). For example, the database may deliver such suggestions to the female subject via an application on a personal communication device. For example, repeated evaluation of calcium may show a decrease over time and the database may generate a suggestion to the female subject to effect one or more lifestyle changes (e.g. administer a calcium supplement, increase intake of diary in the diet, etc.).

In some embodiments, the female subject utilizes the subject interface to access information stored on the database. In some embodiments, the healthcare provider utilizes the healthcare provider interface to access information stored on the database. In some embodiments, various different healthcare providers utilize the healthcare provider interface to access information stored on the database. For example, in some embodiments, 2 or more, or 3 or more, or 4 or more different healthcare providers utilize the healthcare provider interface to access information stored on the database. Such different healthcare providers may be specialists that communicate with the subject and/or the subject's primary different healthcare providers, such specialists including, for example, oncologists, rheumatologists, etc.

In some embodiments, other parties, including health and/or life insurance providers, may utilize the healthcare provider interface to access information stored on the database. For example, health and/or life insurance providers may be provided access to assess insurance eligibility and/or to allow for reduce premiums by de-risking a female subject's insurance via monitoring (e.g. a female subject providing access to the repeated evaluations provided herein may receive lower premiums). For example, data can be transferred to such insurance providers in lieu of physical testing. Also, proof of regular monitoring may be used to assess insurability of a female subject.

In various embodiments, the present methods and/or any evaluation/database of female subject information is used in a healthcare system (e.g. with some of the insurance features described herein) to create a rewards program to offer incentive for women to take monthly samples. For example, a health insurance may monetarily incentivize sample evaluation by offering rebates.

In various embodiments, the present methods and/or any evaluation/database of female subject information is used to disseminate information across patient communities committed to finding cures, including patient support groups and disease-specific organizations/foundations (e.g. American Cancer Society, Komen, Alzheimer's Foundation of America, etc.). In some embodiments, the present methods create disease databases that allow for development of more effective therapeutic options in any of the diseases described herein.

In various embodiments, the present methods and/or any evaluation/database of female subject information is combined with self-measurement of physiological parameters to provide further information of health status, for example, one or more of heart rate, blood pressure, number of steps walked, quality of sleep, calories consumed, and calories burned. In some embodiments, the present methods further comprises evaluating one or more of a pain score, allergies, mood, food/dietary information, health checklists, healthcare records, medications, tests, test results, care plans, and discharge plans. In some embodiments, the present methods are combined with data from activity tracking devices (e.g. FITBIT, Jawbone UP, Nike+ FuelBand, etc.). In some embodiments, the present methods are used in biometric analysis of an athlete. For example, in some embodiments, an athlete may use the present methods to track the progress of recovery from a long-term injury (e.g. a sprain, bone breakage, etc., which may use, by way of non-limiting example, CRP evaluation).

In some embodiments, the database is suitable for database warehousing. In some embodiments, the database is integrated into the female subject's existing electronic medical records. For example, when appropriate the database may be linked with the subject's genetic data/genetic information such as, for example, the sort that may be generated in an oncology patient. In various embodiments, the database is used to create a Continuity of Care Record (CCR). The present invention provides for adding data to the CCR via the present methods and transmitting the data and edited CCR via wireless cell phone communication, Internet, ultrasound, Bluetooth, or near-field communication (e.g. using the database of the present disclosure).

In various embodiments, the present methods allow for improved research and understanding of women's health. For instance, in some embodiments, the present methods improve epidemiological analysis of women's health (e.g. analysis of diseases specific to women, analysis of diseases that progress differently in women than men). Further, in various embodiments, the present methods allow for studies of how women react to therapeutic agents (e.g. in the clinical trial setting, e.g. allowing study of pharmacodynamics and pharmacokinetic parameters of certain agents with females). Accordingly, in some embodiments, the present methods allow for more efficient clinical trial design that is cognizant of gender differences.

In various embodiments, the female subject is menstruating and thus generating sample for evaluation. In some embodiments, the female subject is non-menopausal or recently menopausal. In some embodiments, the female subject may be repeatedly evaluated until pregnancy and resume evaluation post-partum. In these embodiments, the female subject may be monitored for post-partum complications. For instance, the pre-pregnancy data may be used in comparison with post-partum data to monitor a restoration of pre-pregnancy health baselines.

In some embodiments, the female subject has an age in a range of from about 13 years to about 60 years. In some embodiments, the female subject is about 10 years old, or about 15 years old, or about 20 years old, or about 25 years old, or about 30 years old, or about 35 years old, or about 40 years old, or about 45 years old, or about 50 years old, or about 55 years old, or about 60 years old, or about 65 years old.

EXAMPLES

The women's reproductive system is an active environment composed of multiple structures working together. Although each structure is responsible for its own unique function, the systems functions are mediated each month from puberty until menopause by different stages of the menstrual cycle. The process of menstruation occurs for approximately 3-5 days at the beginning of each monthly cycle. The follicles present at the distal tubal opening of the fallopian tube generate a flux of menstrual fluids and mucosal tissue layers throughout the cycle that are ultimately shed with the endometrial lining during menstruation, and secreted as menstrual blood through the cervix, out of the vagina and ultimately discarded. Throughout much of history, menstruation has been accepted as an innate and necessary function of the female reproductive system with little inquiry into the proteomic constituents of menstrual blood native to the females reproductive system. However, in recent years, what we have come to understand about menstrual secretions has changed dramatically. With the accumulation of proteins and cellular debris throughout the menstrual cycle, studies have shown that menstrual blood actually contains a variety of proteins that have promising potential to provide insight into the gynecologic state of the patient. The identification of proteomic biomarkers in menstrual blood offers a unique opportunity to bypass the current limitations in diagnosing gynecologic malignancies such as ovarian cancer by exploiting these monthly secretions during menstruation to evaluate the gynecologic state of both healthy and diseased individuals. As a result of the shared circulation between systemic circulation and reproductive health, other biomarkers can be found within menstrual blood that are indicative of general well-being and health outside of the female reproductive system.

A purpose of this Example is to deliver a point-of-care diagnostic tool to women from "bench to bedside". With the progress of technology and proteomic analysis comes the opportunity to develop tools accurate and effective enough to replace the current and ineffective diagnostic protocols that use biomarkers to screen for malignancies at the proximal level of the reproductive system, in addition to indications of malignancies throughout the rest of the bod and/or the general well-being of the female.

The Example in phase I focuses on the validation of the correlation of biomarkers found in menstrual blood to biomarkers in venous circulation, important because this confirmation of specific biomarkers present in menstrual blood will be vital to constructing trials described elsewhere herein, and to define statistically significant elevations of those specific biomarkers found in menstrual blood throughout the duration of the period. The quantitative assessment of these marked elevations will take precedence during the production of subsequent clinical trials described elsewhere herein using identified biomarkers in menstrual blood for early detection of ovarian cancer. CA-125 biomarker elevations will be used as a benchmark against any biomarkers validated in this study, along with subsequent correlation and justification of additional biomarker elevations in patients with early stage ovarian cancer. Additional trials will be conducted that will be inclusive of the remaining number of biomarkers found in menstrual blood, similar to the trials described above as they pertain to malignancies outside the reproductive system and/or general well-being. This panel may be implemented into a personal point-of-care device, to be used monthly by women interested in monitoring their gynecologic health, general health and/or well-being.

The timing of diagnosis of ovarian cancer plays a crucial role in increasing the chances of survival. However, due to the latent nature of the symptoms that accompany ovarian cancer, diagnosis is often at later stages when the cancer has metastasized distant to the ovary and the chance of survival is 17%. The diagnostic protocols currently in use require appointments, blood draws, biopsies and other painful and inconvenient procedures that contribute to delayed diagnosis and high mortality rates. An objective of this Example is to validate a panel of novel biomarkers found in menstrual blood that can be integrated into an "at home" proteomic point-of-care device, to screen for ovarian cancer. Other studies will be conducted that will be inclusive of other proteomic constituents of menstrual blood as they relate to cellular processes associated to other diseases and/or malignancies outside of the reproductive system and/or general well-being. Having a tool whose function is to provide insight into the unknown proteomic changes that occurs prior to the onset of malignancies and/or diseases can provide many benefits to women. By using this device every month, the collection of longitudinal data of biomarkers will give both women and physicians a more accurate diagnostic impression of a woman's gynecologic health, health and well-being using menstrual blood.

Despite many advances in the field of screening diagnostic methodologies for cancer, only 15% of all ovarian cancers are found at an early stage when the 5-year relative survival rate is 92%. Unfortunately, almost 70% of women with the common epithelial ovarian cancer are not diagnosed until the disease is advanced in stage when the relative 5-year survival rate is 17%. Predictive and preemptive diagnostics capable of detecting cancer at an early stage would likely improve long-term survivability rates. Specifically for ovarian cancer, the most common cause of mortality as a result of late stage ovarian cancer diagnosis is disseminated carcinomas. Despite decades of research, no diagnostic methodology or screening protocol can produce consistent and accurate diagnosis at an early stage when the chances of survival are high. There are proteomic-screening tests that are capable of detecting ovarian cancer, but there has been no progress in the development of a diagnostic screening tool capable of early stage diagnosis as a result of numerous limitations. Important limitations associated with mortality and morbidity stem from the ambiguity in the overexpression of the CA-125 protein during different stages of ovarian cancer, and variances in the expression of this protein amongst individuals during different phases of menstrual cycle. Additional limitations include the latent nature of symptoms associated with ovarian cancer and other malignancies and/or diseases outside of the reproductive system; and inconvenient and painful blood draws and lab procedures that serve no role in increasing patient accountability for their own health.

There is a population of biomarkers within menstrual blood that will overcome these hurdles. For example, activin A and follistatin have an active role in endometrial function and the quantitative assessment of these proteins in menstrual serum illustrates the potential for the use of Activin A and Follistatin as tumor markers for ovarian cancer. There may be a reduction in false-positives while screening for ovarian cancer when Follistatin was combined with CA-125. Therefore, an object of this Example is to provide an at-home diagnostic tool that primarily tests for protein biomarkers using menstrual blood, which can be collected each month, creating a log of longitudinal data that offers more accurate and personalized diagnostics to screen for ovarian cancer. For instance, the following hypotheses are investigated:

Biomarkers found in menstrual fluid are a more accurate medium than peripheral blood to test for neoplastic gynecologic pathologies and other diseases of the female reproductive system due to menstrual fluid's intimate relationship with the female reproductive organs.

Activin A and Follistatin are examples of many biomarkers found in menstrual blood that are statistically superior to biomarkers found in peripheral blood to screen for ovarian cancer and other diseases of the reproductive tract.

Biomarkers found in menstrual blood are also indicative of diseases or general well-being outside of the female reproductive system. Illustrative specific aims include: (1) showing that menstrual fluid can be used to screen for ovarian cancer using statistical and quantitative assessments of biomarkers. An exemplary milestone is elevation of biomarkers associated to ovarian cancer found in menstrual blood is correlated to elevations of biomarkers in peripheral blood.; (2) determining the degree of correlation between Activin A and Follistatin in menstrual blood in relation to ovarian cancer. An exemplary milestone is Activin A and Follistatin are elevated in menstrual blood in patients with ovarian cancer.

The use of a diagnostic screening tool that uses menstrual blood to test for biomarkers associated with ovarian cancer should greatly improve patient-accountability, patient quality of life, prognosis of the disease, and reduce the economic burden that accompanies cancer treatment. The device will benefit those by offering personalized longitudinal data collection of biomarkers using menstrual blood to screen for ovarian cancer from a point-of-care device that can be used from the privacy of the patient's home. This shift of more personalized care through portable, modern and private screening diagnostic tool using biosensors and the natural process of menstruation will likely result in more patient accountability and a decrease in mortality as a result of late diagnostics.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for evaluating one or more disease or health related biomarkers in a female subject, comprising: (a) obtaining a first sample of the female subject's menstrual fluid on a collection device; (b) detecting a presence, absence, or level of the one or more disease- or health-related biomarkers in the first sample; and (c) obtaining a subsequent menstrual fluid sample and sampling the subsequent menstrual fluid sample and detecting a presence, absence, or level of the one or more disease- or health-related biomarkers in the subsequent sample and wherein the method comprises examining the biomarkers detected in the first sample and subsequent sample to determine a presence, absence, or level of the one or more disease or health related biomarkers and wherein the biomarkers detected in the sample and subsequent sample are Follistatin and Activin A biomarkers.

2. A method for evaluating one or more disease- or health-related biomarkers in a female subject, comprising: (a) obtaining a first sample of the female subject's menstrual fluid; (b) detecting a presence, absence, or level of the one or more disease- or health-related biomarker proteins in the first sample; and wherein the method further comprises obtaining a subsequent menstrual fluid sample and detecting a presence, absence, or level of the one or more disease- or health-related biomarker protein in the subsequent sample; and wherein the one or more disease- or health related biomarkers detected in the first sample and subsequent sample are Follistatin or Activin A biomarker proteins, which provide baseline or trend health information.

3. A method for evaluating one or more disease- or health-related biomarkers in a female subject, comprising: (a) obtaining a first sample of the female subject's menstrual fluid; (b) detecting a presence, absence, or level of the one or more disease- or health-related biomarker proteins in the first sample; wherein the method further comprises obtaining a subsequent menstrual fluid sample and detecting a presence, absence, or level of the one or more disease- or health-related biomarker proteins in the subsequent menstrual fluid sample; and wherein the method comprises examining the first sample and subsequent sample for Follistatin and Activin A biomarker proteins as the disease- or health-related biomarker proteins, which provides baseline or trend health information.

* * * * *